US011602310B2

(12) United States Patent
Clasbrummel (10) Patent No.: US 11,602,310 B2
(45) Date of Patent: Mar. 14, 2023

(54) MEDICAL IMPLANT AND METHOD OF DIAGNOSING AND/OR TREATING INFLAMMATORY TISSUE CONDITIONS

(71) Applicant: Bernhard Clasbrummel, Stuttgart (DE)

(72) Inventor: Bernhard Clasbrummel, Stuttgart (DE)

( * ) Notice: Subject to any disclaimer, the term of this patent is extended or adjusted under 35 U.S.C. 154(b) by 855 days.

(21) Appl. No.: 16/370,162

(22) Filed: Mar. 29, 2019

(65) Prior Publication Data
US 2019/0298263 A1 Oct. 3, 2019

(30) Foreign Application Priority Data
Mar. 30, 2018 (DE) ................... 10 2018 204 949.1

(51) Int. Cl.
*A61B 5/00* (2006.01)
*A61B 5/07* (2006.01)
(Continued)

(52) U.S. Cl.
CPC ............ *A61B 5/686* (2013.01); *A61B 5/0071* (2013.01); *A61B 5/0084* (2013.01); *A61B 5/076* (2013.01); *A61B 5/4528* (2013.01); *A61B 5/4571* (2013.01); *A61B 5/4839* (2013.01); *A61B 5/4851* (2013.01); *A61F 2/32* (2013.01); *A61F 2/38* (2013.01); *A61F 2/3859* (2013.01); *A61F 2/40* (2013.01); *A61F 2/42* (2013.01); *A61L 27/14* (2013.01); *A61N 1/3702* (2013.01);
(Continued)

(58) Field of Classification Search
CPC ..... A61B 5/686; A61B 5/0071; A61B 5/0084; A61B 5/076; A61B 5/4528; A61B 5/4571; A61B 5/4839; A61B 5/4851; A61B 5/0031; A61B 5/0036; A61B 2560/0214; A61B 2562/0233; A61F 2/32; A61F 2/38; A61F 2/3859; A61F 2/40; A61F 2/42; A61F 2/48; A61F 2002/183; A61F 2002/3009; A61F 2002/3067; A61F 2002/30698; A61F 2250/0002; A61F 2310/00179; A61F 2310/00329; A61L 27/14; A61N 1/3702; A61N 1/37211
USPC ....................................................... 600/302
See application file for complete search history.

(56) References Cited

U.S. PATENT DOCUMENTS

| 8,216,173 B2 * | 7/2012 | Dacey, Jr. .......... A61B 5/14503 604/9 |
| 8,702,640 B2 * | 4/2014 | Dacey, Jr. ................ A61F 2/30 604/9 |

(Continued)

FOREIGN PATENT DOCUMENTS

| DE | 10 2007 028 659 A1 | 12/2008 |
| DE | 10 2007 034 042 A1 | 1/2009 |

(Continued)

OTHER PUBLICATIONS

Extended European Search report dated Jul. 23, 2019, of counterpart European Application No. 19165548.9.

(Continued)

*Primary Examiner* — May A Abouelela
(74) *Attorney, Agent, or Firm* — DLA Piper LLP (US)

(57) ABSTRACT

A medical implant includes a sensor that detects electromagnetic waves; and a data transmission unit that can wirelessly transmit data supplied by the sensor to a receiving unit.

11 Claims, 3 Drawing Sheets

(51) Int. Cl.
  *A61F 2/32*  (2006.01)
  *A61F 2/38*  (2006.01)
  *A61F 2/40*  (2006.01)
  *A61F 2/42*  (2006.01)
  *A61L 27/14*  (2006.01)
  *A61N 1/37*  (2006.01)
  *A61F 2/18*  (2006.01)
  *A61F 2/30*  (2006.01)
  *A61N 1/372*  (2006.01)
  *A61F 2/48*  (2006.01)

(52) U.S. Cl.
  CPC .......... *A61B 5/0031* (2013.01); *A61B 5/0036* (2018.08); *A61B 2560/0214* (2013.01); *A61B 2562/0233* (2013.01); *A61F 2/48* (2021.08); *A61F 2002/183* (2013.01); *A61F 2002/3009* (2013.01); *A61F 2002/3067* (2013.01); *A61F 2002/30698* (2013.01); *A61F 2250/0002* (2013.01); *A61F 2310/00179* (2013.01); *A61F 2310/00329* (2013.01); *A61N 1/37211* (2013.01)

(56) References Cited

U.S. PATENT DOCUMENTS

| | | | | |
|---|---|---|---|---|
| 8,734,718 | B2* | 5/2014 | Dacey, Jr. | A61N 5/0624 422/23 |
| 9,005,263 | B2* | 4/2015 | Boyden | A61L 2/0011 607/96 |
| 9,451,919 | B2* | 9/2016 | Roche | A61B 5/4528 |
| 2002/0077556 | A1 | 6/2002 | Schwartz | |
| 2006/0047283 | A1* | 3/2006 | Evans, III | A61B 5/412 623/20.2 |
| 2008/0058587 | A1* | 3/2008 | Boyden | A61N 5/01 600/104 |
| 2008/0306324 | A1* | 12/2008 | Bonutti | A61F 2/38 600/12 |
| 2008/0306359 | A1* | 12/2008 | Zdeblick | H02J 50/20 604/93.01 |
| 2009/0024054 | A1 | 1/2009 | Lazarus | |
| 2010/0189659 | A1 | 7/2010 | Fehre | |
| 2010/0204802 | A1 | 8/2010 | Wilson | |
| 2010/0234792 | A1* | 9/2010 | Dacey, Jr. | A61B 5/145 604/8 |
| 2011/0093008 | A1* | 4/2011 | Mayer | A61B 90/98 606/213 |
| 2012/0190989 | A1* | 7/2012 | Kaiser | A61B 5/08 600/300 |
| 2014/0147802 | A1* | 5/2014 | Naldoni | A61N 5/0603 433/29 |
| 2014/0288412 | A1* | 9/2014 | Schwartz | A61B 90/39 600/407 |
| 2015/0196225 | A1* | 7/2015 | Rusu | A61B 5/0537 600/301 |
| 2015/0196253 | A1* | 7/2015 | Mayer | A61B 5/076 600/302 |
| 2015/0212175 | A1* | 7/2015 | Lee | A61B 5/14546 600/302 |
| 2016/0066850 | A1* | 3/2016 | Brockway | A61N 1/37229 600/377 |
| 2016/0192878 | A1 | 7/2016 | Hunter | |
| 2018/0049891 | A1* | 2/2018 | Termanini | A61F 2/4607 |
| 2018/0085605 | A1* | 3/2018 | Maharbiz | A61B 8/0808 |
| 2018/0117331 | A1* | 5/2018 | Kuzniecky | A61B 5/686 |
| 2018/0125366 | A1* | 5/2018 | Lucey | A61F 2/4657 |
| 2018/0165566 | A1* | 6/2018 | Rogers | G06K 19/0716 |
| 2019/0175015 | A1* | 6/2019 | Adams | A61L 31/088 |
| 2019/0247664 | A1* | 8/2019 | Irazoqui | A61N 1/3611 |
| 2020/0315540 | A1* | 10/2020 | Jones | A61B 5/6873 |
| 2020/0383808 | A1* | 12/2020 | Li | A61F 2/82 |

FOREIGN PATENT DOCUMENTS

| | | |
|---|---|---|
| DE | 20 2015 009 423 U1 | 8/2017 |
| WO | 97/33513 A1 | 9/1987 |
| WO | 2008/035089 A1 | 3/2008 |
| WO | 2014/209916 A1 | 12/2014 |

OTHER PUBLICATIONS

Dibartola, Alex C. etal, "Biofilms in Orthopedic Infections: A Review of Laboratory Methods." *APMIS 125: 418-428*, Apr. 2017. http://www/researchgate.net/publication/312374414.

Dartnell, L., Roberts, T., Moore, G., Ward, J.M., Muller, J. "Fluorescence Characterization of Clinically-Important. Bacteria." *PLOS one*, Sep. 30, 2013, http://journals.plos.org/plosone/article?id=10.1371/journal.pone.0075270, pp. 1-10.

* cited by examiner

MEDICAL IMPLANT AND METHOD OF DIAGNOSING AND/OR TREATING INFLAMMATORY TISSUE CONDITIONS

TECHNICAL FIELD

This disclosure relates to a medical implant intended for implantation in a human or animal body and a method of diagnosing and/or treating inflammatory tissue conditions in a tissue adjacent to the implant.

BACKGROUND

Insertion of implants into a human or animal body usually requires surgical intervention and in the following wound healing. During wound healing, there can be various complications that can have a negative influence on the healing process. In the postoperative healing process, especially immediately after the implant has been inserted, inflammation may occur in tissue adjacent to the implant. Such inflammations occur in 1-2% of all cases and are usually caused by bacteria. If they are not detected at an early stage, follow-up interventions may be necessary. In severe cases, it may even be necessary to remove the implant.

As a common rule, the earlier inflammations are detected, the better they can be repressed. However, this is difficult in implants. Visual monitoring of the healing process is usually not possible and inflammation markers such as C-reactive protein (CRP) and inflammation parameters such as an increase in body temperature or an increase in the number of leukocytes are too unspecific.

WO 2014/209916 A1 and WO 2008/035089 A1 disclose implants with sensors for the detection of inflammatory conditions. The sensors can be physical sensors such as pressure and temperature sensors or chemical or biological sensors. The sensors can be controlled contactless.

There is a need to better detect inflammatory tissue states in tissue adjacent to the implant and in body fluids, for example, synovial fluid or bone tissue, as early as possible after the insertion of an implant.

SUMMARY

I provide a medical implant including a sensor that detects electromagnetic waves; and a data transmission unit that can wirelessly transmit data supplied by the sensor to a receiving unit.

I also provide a method of diagnosing and/or treating inflammatory tissue including the sensor of the implant detecting electromagnetic waves whose properties depend on the vicinity of an implant or on the condition of tissue adjacent to the implant with a sensor in the implant, and wirelessly transmitting data supplied by the sensor with a data transmission unit to a receiving unit.

I further provide a medical implant including a sensor that detects electromagnetic waves and includes at least one electronic component designed for detection of electromagnetic waves; a data transmission unit that wirelessly transmits data supplied by the sensor to a receiving unit; and a light source capable of emitting light in a range of the electromagnetic spectrum visible to a human eye and/or a radiation source capable of emitting electromagnetic radiation outside the visible range, IR radiation or UV radiation; and at least one controller that controls the functions of the sensor and/or the data transmission unit; wherein the sensor and the data transmission unit and the controller and the light source and/or the radiation source are located in at least one cavity in the implant.

DETAILED DESCRIPTION

My implant is intended for implantation in a human or animal body. It is characterized by the following features:
 a. a sensor to detect electromagnetic waves; and
 b. a data transmission unit that can wirelessly transmit data supplied by the sensor to a receiving unit.

The sensor is designed such that it can directly or indirectly detect possible changes in the properties of body tissue adjacent to the implant or in body fluids such as the aforementioned synovial fluid, in particular formation of inflammatory tissue states. Preferably, the sensor is also designed to detect changes on surfaces of the implant and in the immediate vicinity of the implant. In bacterial inflammation, biofilms are very quickly deposited on surfaces of the implant. These usually include a slime layer (film) in which microorganisms are embedded. Such biofilms can be easily detected with the sensor. The arrangement of the sensor within the implant allows—if necessary—even live monitoring of the healing process. If an inflammation develops, it can be detected as it develops. This enables early countermeasures to be taken.

The data transmission unit is preferably a miniaturized device that can transmit data wirelessly using modulated electromagnetic waves in the radio frequency range. For example, the device can be a Bluetooth, WLAN, Zigbee, GSM, CDMA, UMTS or LTE chip or the like.

The receiving unit is usually a data processing device such as a computer having a receiving chip able to communicate with the data transmission unit.

The implant can be single or multi-part implant. In a multi-part implant, it may be preferable for a sensor system and a data transmission unit to be integrated in each of the parts.

In a multi-part implant, it is preferred that the sensor is designed for the purpose and/or arranged within one of the implant parts such that, in particular, interfaces between the parts of the implant parts can be observed.

Particularly preferably, the implant is characterized by the following additional features:
 a. at least one cavity in which the sensor and the data transmission unit are arranged, and
 b. designed such that the electromagnetic waves can reach the sensor located in the cavity.

It is advisable to position the sensor and the data transmission unit in one or more cavities within the implant. It is possible that a component of the sensor or the data transmission unit limits the cavity to the outside. It is also possible that the sensor and the data transmission unit are located in different cavities within the implant.

Preferably, it is not intended to remove the sensor and the data transmission unit from the implant after healing. Rather, it is generally intended that the sensor and the transmission unit remain permanently in the implant. For this reason it is preferred that the cavity or cavities are hermetically sealed to the outside.

It is necessary that the sensor is able to receive the electromagnetic waves to be detected. Therefore, at least those parts of the implant located between the sensor and the surrounding tissue should preferably be able to be penetrated by electromagnetic waves. The implant must therefore at least partially consist of a material that is transparent to electromagnetic waves.

Particularly preferably, the implant is characterized by at least one of the following additional features:
  a. consists of at least in part of a glass, in particular of a transparent glass,
  b. consists of at least in part of a glass ceramic,
  c. consists of at least in part of a ceramic, and
  d. consists of at least in part of a plastics material, for example, a polyolefin such as polyethylene.

Generally, these materials are transparent to waves in wide ranges of the electromagnetic spectrum and therefore meet the above requirements. In many instances, however, the use of a plastic as a material transparent to electromagnetic waves is particularly preferred.

As the glass, a so-called bioglass, which is usually highly compatible with body tissue, can be used.

A glass ceramic is a material produced from a glass melt by controlled crystallization. Generally, a glass ceramic is characterized by high transmittance of infrared radiation.

With regard to the plastics material, plastics with a high wear resistance and a high compatibility with body tissue are preferred, in addition to the already mentioned polyolefins. In particular, fluorinated polymers such as Teflon and polyetherketones such as polyetheretherketone are suitable.

The implant particularly preferably comprises a metallic supporting structure, e.g. made of titanium or stainless steel, which is enclosed by the glass, glass-ceramic or plastic in certain areas or completely.

It is preferred that the implant comprises in combination metallic components, components made of plastic and components made of glass ceramic or glass.

It is preferred that the implant is characterized by at least one of the following additional features:
  a. the sensor comprises at least one electronic component designed for detection of electromagnetic waves within a limited wavelength range, in particular in the visible range of the electromagnetic spectrum and/or in the infrared range,
  b. the at least one electronic component comprises a photoresistor, a photodiode, a photo transistor or other photosensitive electronic component,
  c. the electronic component is a photosensitive electronic image sensor designed to detect electromagnetic waves, and
  d. the at least one photosensitive electronic image sensor is a CCD sensor or a CMOS sensor.

Particularly preferably, the sensor is designed to detect electromagnetic waves in the frequency range of 200 nm to 700 nm, particularly preferably 200 nm to 550 nm. Many bacteria give a fluorescence response within this frequency spectrum when stimulated by light.

According to the immediately preceding c. and d., the sensor is designed to generate an image, in particular a two-dimensional image. Therefore, it can be preferred that the electronic component is an electronic image converter. The electronic component can be designed both to receive electromagnetic radiation from the visible range and receive infrared radiation. In the first example, it can generate a photographic image, in the second, a thermal image. This makes it possible to visually monitor the healing process.

Preferably, the electronic component is designed to generate 2D and/or 3D images.

Inflammatory tissue states are often accompanied by local warming. When an implant equipped with the electronic component designed to receive infrared radiation is implanted into a body, the component can provide a thermal image of body tissue adjacent to the implant at regular intervals. If the tissue changes into an inflamed state, the associated warming is immediately detected.

If the component is designed to receive electromagnetic radiation from the visible range, the sensor system may include one or more lenses to focus incident light.

The acquisition of an image is not always necessary or expedient, as will be explained in connection with my method. Rather, for the detection of inflammatory tissue states, it may also be sufficient to detect waves with only one wavelength (and not an entire range of the electromagnetic spectrum) and monitor them for changes in intensity. For this it is sufficient if a sensor is used in accordance with immediately preceding features a. and b.

It may also be preferred that the implant is characterized by at least one of the following additional features:
  a. at least one control unit that controls the functions of the sensor and/or the data transmission unit.
  b. the control unit is designed to cause the data supplied by the sensor to be forwarded directly to a receiving unit via the data transmission unit,
  c. the control unit is designed to store the data supplied by the sensor and transmit them to the data transmission unit at a later time,
  d. the control unit is designed to process, for example, compress, compare and/or combine, the data supplied by the sensor with previously collected data or stored reference data, and
  e. the control unit is located in the cavity containing the sensor or in another cavity within the implant.

In the simplest example, the control unit is an integrated circuit (IC). If necessary, the control unit is combined with the sensor and/or the data transmission unit to an integrated circuit.

Preferably, the sensor is activated and deactivated via the control unit. This can be done in response to an external signal, but it is also possible for the control unit to automatically activate the sensor, for example, at regular intervals, and store the recorded data in a data buffer until it is called up later.

Compression of the data supplied by the sensor can be particularly useful before their transmission by the data transmission unit.

Particularly preferably, the control unit can also carry out an initial evaluation of the supplied data and, for example, only send a warning signal to the receiver via the data transmission unit in the event of a change or detected inflammatory tissue condition.

In many configurations, the implant is characterized by at least one of the following additional features:
  a. a light source is capable of emitting light in the range of the electromagnetic spectrum visible to the human eye, b. a radiation source is capable of emitting electromagnetic radiation outside the visible range, in particular IR radiation or UV radiation,
c. the light and/or radiation source is coupled to the control unit which controls its functions, and
d. the light and/or radiation source is located in the cavity containing the sensor, the cavity containing the control unit or in another cavity within the implant.

The light source according to feature a. is preferably a common light or flash light source. LED light sources are preferred as light sources. The light source is used in particular in combination with one of the described electronic image converters and serves to improve the conditions to generate the photographic image. Light emitted by the light source can be partially reflected by the immediate vicinity of the implant, for example, by tissue adjacent to the implant. The reflected light can be detected by the sensor.

The radiation source according to features b. to d. may be an infrared LED or a UV LED, for example. These radiation sources can be used, for example, within the method described below, to detect a marker or for disinfection.

Particularly preferably, a radiation source in accordance with feature b. is used which is capable of emitting radiation in the frequency range of 10 nm to 400 nm, particularly preferably 100 nm to 350 nm. When excited with electromagnetic radiation in this frequency range, many bacteria give a fluorescence response within the above-mentioned frequency spectrum. In particular, radiation at the shortwave end of the spectrum is suitable for killing bacteria, i.e. for the disinfection mentioned above.

Further preferably, the implant is characterized by at least one of the following additional features:
a. at least one energy source supplies electrical energy to the sensor and the data transmission unit and, where appropriate, to the control unit and/or the light and/or radiation source,
b. the at least one energy source comprises an electrochemical cell,
c. the at least one energy source comprises a capacitor,
d. the at least one energy source comprises an induction coil or coupling coil,
e. the at least one energy source comprises an energy converter, and
f. the energy source is located in the cavity containing the sensor, the cavity containing the control unit, the cavity containing the light and/or radiation source or in another cavity within the implant.

In the electrochemical cell version, the energy source is preferably designed such that it can supply the sensor and the components of the implant coupled to the sensor with electrical energy for at least 24 hours. This ensures that the healing process can be monitored without interruption, at least immediately after implantation.

The capacitor may be required in particular in combination with the light source described above, especially if it is a flash light source.

If the energy source is designed as an induction coil/coupling coil, energy can be transferred contactlessly from outside the implant. The implant particularly preferentially comprises a combination of the induction coil/coupling coil and the electrochemical cell, the latter being preferably designed to be rechargeable in this case.

In the context of this application, an energy converter is understood to be a component that enables generation of electrical energy from mechanical energy and/or thermal energy. The energy converter can generate electrical energy from ambient temperature, vibrations, movement and pressure. For example, components can be used as energy converters in which mechanical pressure is converted into electrical voltage by a piezoelectric effect.

Preferably, the implant comprises a combination of the energy converter and the electrochemical cell, whereby the latter may preferably be designed to be rechargeable.

It is preferred that the implant is characterized by the following additional feature: a. the induction coil/coupling coil is part of the data transmission unit.

Preferably, the induction coil is designed for inductive data transmission. This allows data and the required energy to be transmitted together without contact. Such couplings between energy supply and data transmission are already in use in many applications, as an example cochlear implants and RFID technology can be mentioned in this context.

It is further preferred that the implant is characterized by at least one of the following additional features:
a. diagnostic substance detects inflammation,
b. the diagnostic substance is positioned on an outer side of the implant, and
c. a depot contains the diagnostic substance.

The diagnostic substance preferably comprises a coupling molecule that specifically couples or binds to a molecular structure formed in the tissue as a result of inflammation. The molecular structure may be an individual molecule, a molecular assembly or a molecular surface structure. The coupling molecules are preferentially provided with a biochemical marker so that an accumulation of coupling molecules in inflamed tissue or in a body fluid or on a surface of the implant can be detected.

Preferably, markers are used that absorb electromagnetic waves such as visible light or X-rays and can be detected, for example, by their absorption or emission spectrum. Marker dyes that absorb in the near infrared (NIR) are particularly preferred. Fluorescent dyes are particularly preferred because they usually absorb in a wavelength range different from their fluorescence spectrum so that the fluorescent light emitted by them can easily be filtered out of the excitation light.

For diagnostic purposes, the diagnostic substance can be released from the depot, for example, in response to a signal from the control unit. In the event of inflammation, it will accumulate at the site of inflammation. When excited with an electromagnetic wave, a fluorescent dye used as a marker will emit electromagnetic waves of a longer wavelength, which can be detected, for example, by the sensor of the implant.

It is further preferred that the implant is characterized by at least one of the following additional features:
a. an active substance treats inflammation,
b. the active substance is applied on an outer side of the implant, and
c. a depot contains the active substance.

The presence of the active substance enables not only the diagnosis of inflammations, but also their immediate treatment. For example, the depot can connect to the control unit and release the drug upon a signal from the control unit.

Particularly preferably, the implant is characterized by at least one of the following additional features:
a. the implant comprises an artificial joint, and
b. the joint is selected from the group consisting of the shoulder joint, elbow joint, wrist joint, hip joint, knee joint and ankle joint.

The implant is therefore preferably an endoprosthesis intended to remain permanently in the body and replaces a damaged joint in whole or in part.

Particularly preferably, the implant is an artificial hip joint. An artificial hip joint usually comprises a hip stem, a head part fixed to it and designed as a ball head, and a hip socket (acetabulum) in which the ball head can move. The hip stem preferably consists of a metal such as titanium, the ball head prefers ceramic, glass or glass-ceramic. The acetabulum is preferably made of polyethylene with a metallic supporting structure, for example, titanium or a similar suitable metal. In the latter example, a plastic inlay, in particular the polyethylene mentioned above, or a ceramic inlay, is preferably arranged between the head part and the acetabulum. The sensor of the implant is preferably located inside the head part.

Generally, the sensor is preferably located in areas of the implant in the immediate vicinity of the joint connections or in areas to be connected to or into existing bone. Inflammations such as a bacterial infection of the joint cavity or osteitis are difficult to diagnose, an early diagnosis can in many instances ensure implant retention.

The method of diagnosing and/or treating inflammatory tissue includes the following steps a. and b.:
a. the sensor of the implant is used to detect electromagnetic waves whose properties depend on the vicinity of the implant, in particular on the condition of tissue adjacent to the implant, and
b. data supplied by the sensor are wirelessly transmitted by the data transmission unit to the receiving unit.

The implant has to be implanted into a human or animal body before steps a. and b.

The principle underlying the method has already been explained in the context of the description of the implant. Accordingly, it is apparent that the condition of the tissue adjacent to the implant to be detected is in particular an inflammatory condition.

There are two particularly preferred examples of the method.

In a first particularly preferred example of the method, the method comprises the following additional steps:
a. the vicinity of the implant, in particular the tissue adjacent to the implant and/or a body fluid in contact with the implant, is exposed to electromagnetic radiation, in particular in the visible range of the electromagnetic spectrum and/or in the infrared range,
b. the electromagnetic radiation is emitted from a source of light and/or radiation inside the implant or outside the human or animal body (and thus from outside the implant), in particular from one of the light and/or radiation sources described above, and
c. electromagnetic waves emitted or reflected from the vicinity, in particular from a tissue and/or body fluid, are detected by at least one light-sensitive electronic image sensor and converted into an image transmitted to the receiving unit by the data transmission unit.

In this example, the vicinity is diagnosed by generating a photographic image or a thermal image of the vicinity, such as tissue or body fluid.

In a second particularly preferred example of the method, the method comprises the following additional steps:
a. the vicinity of the implant, in particular the tissue adjacent to the implant and/or a body fluid in contact with the implant, is brought into contact with a biochemical marker to detect inflammation,
b. the vicinity of the implant, in particular the tissue adjacent to the implant and/or the body fluid, is exposed to electromagnetic radiation that overlaps with an absorption and/or fluorescence spectrum of the marker, and
c. the electromagnetic radiation is emitted from a source of light and/or radiation inside the implant or outside the human or animal body (and thus from outside the implant).

According to this example, it is not necessary to take an image. To detect inflammatory tissue states, it is sufficient to detect the electromagnetic waves emitted by the marker or to track the intensity of electromagnetic waves absorbed by the marker. The marker and its function have already been explained in detail. It is a preferred component of the diagnostic substance described above.

It should be emphasized that the principle underlying this disclosure is basically applicable to all implantable objects and not only to the endoprostheses mentioned above. For example, the implant may also be a pacemakers or an implantable hearing aid.

Further features, details and benefits can be taken from the appended claims and the abstract, both of which are made by reference to the contents of the description, from the following description of preferred examples and from the drawings.

Figure 1:
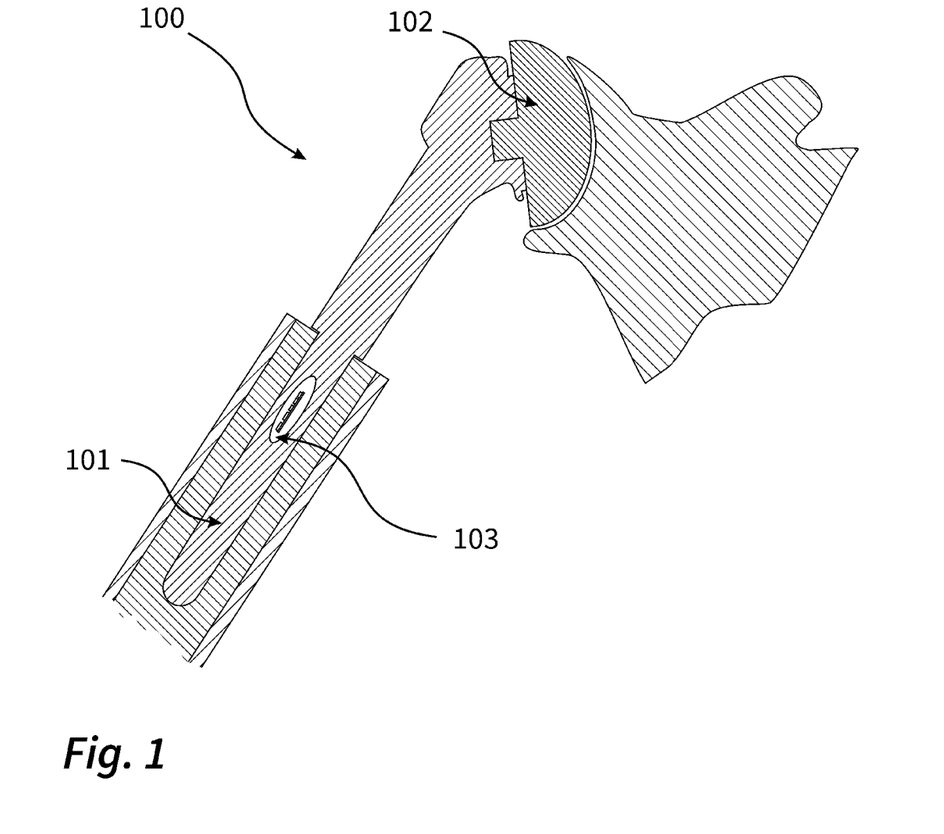
FIG. 1 is a schematic sectional view of an endoprosthesis of an implant for the replacement of a human humeral head.

The implant 100 shown in FIG. 1 comprises a modular base with a bone fixation shaft 101 arranged in the medullary cavity of a resected humerus, and a head portion 102 attached to a shoulder joint socket on a shoulder blade. For the sake of clarity, only the relevant components of the implant are shown. Functional partial elements such as soft tissue fixation mechanisms, e.g. for stretch and abductor soft tissue, are not shown. The bone fixation shaft 101 consists of glass parts and contains the sensor as shown in FIG. 2.

Figure 2:
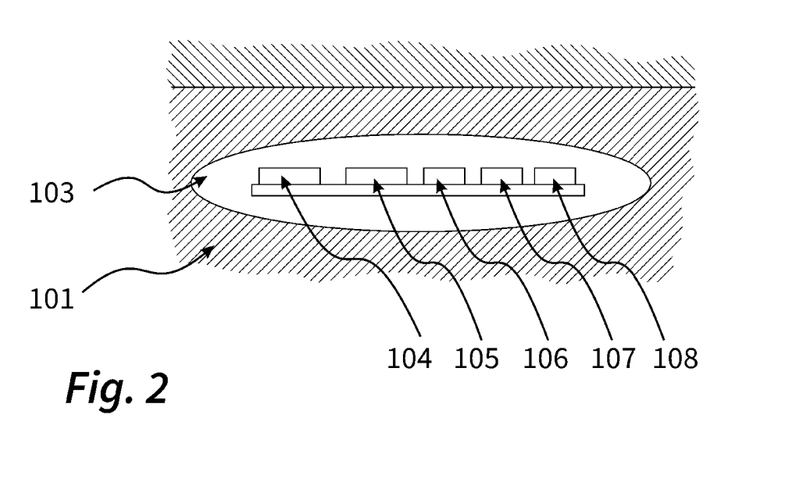
FIG. 2 is a schematic sectional view of a cavity in the bone fixation shaft of the implant from FIG. 1, in which a data transmission unit and a light source are arranged in addition to a sensor.

As shown in FIG. 2, the implant 100 has a cavity 103 within the bone fixation shaft 101. In this cavity, an electronic image sensor as sensor 104 is, the light source 105, an IC as the control unit 106, the data transmission unit 107 and the battery 108 are arranged on a circuit board 109. The battery 108 can be charged via an integrated induction coil (not shown). The electronic image sensor 104, the light source 105 and the data transmission unit 107 are each coupled to the IC 106 that can control their functions.

The electronic image sensor 104 is designed to generate a two- or three-dimensional image of the surrounding tissue. The light source 105 can be used to adjust the lighting conditions during image acquisition. The data supplied by the image sensor 104 is transmitted to a receiver via a Bluetooth protocol using the data transmission unit 107.

Figure 3:
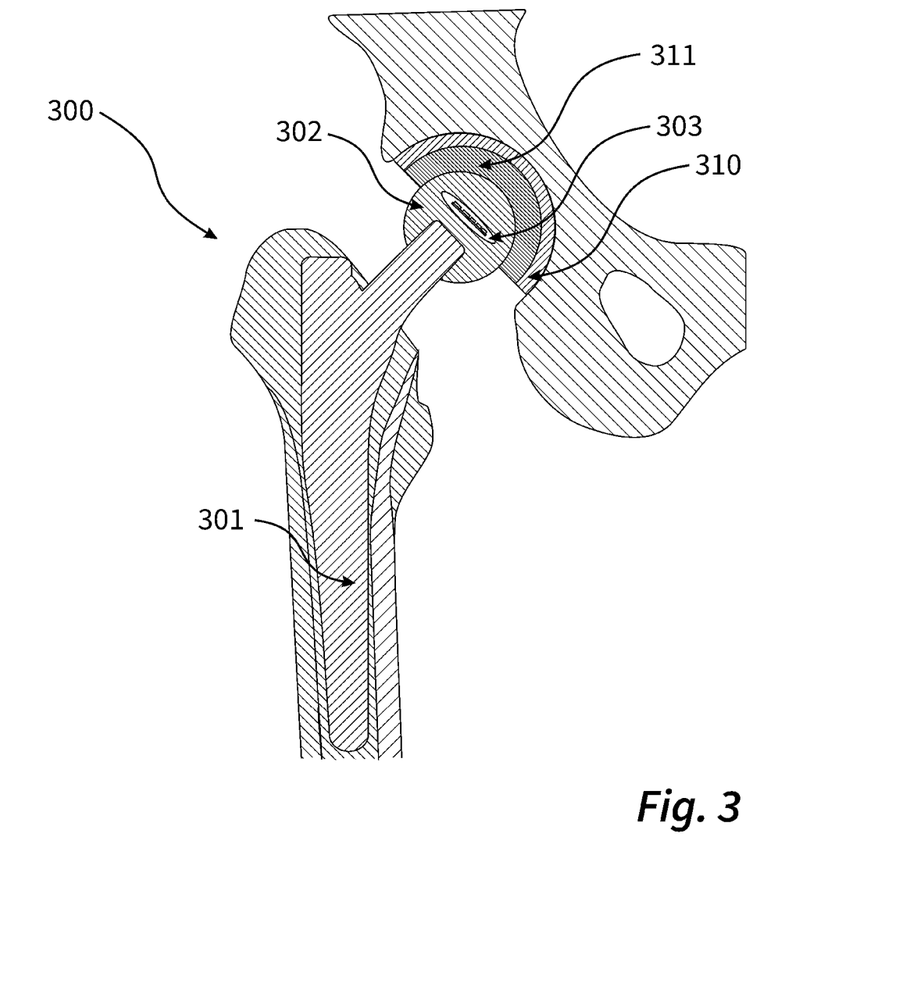
FIG. 3 is a schematic sectional view of an artificial hip joint.

The implant 300 shown in FIG. 3 comprises a modular basic body with a hip stem 301 made of titanium, which is fixed in the illustration in a femur, and a head part 302 designed as a ball head and applied to hip socket 310. The head part 302 essentially consists of a transparent glass body in which a cavity 303 is arranged, and in which the same sensor and the same electronic components are arranged as in the cavity 103 of the implant 100. The hip socket 310 is preferably made of titanium. An inlay 311 made of ultra-high molecular polyethylene is inserted between the acetabulum 310 and the head part 302 and serves as a sliding surface.

By the image sensor arranged in the cavity 303, individual photographic shots, if necessary even film shots of the surfaces of the head part 302 and the inlay 311 as well as of the interfaces between the head part 302 and the inlay 311 can be produced. For example, formation of a biofilm on one of these surfaces or interfaces as a result of inflammation can be detected.

Figure 4:
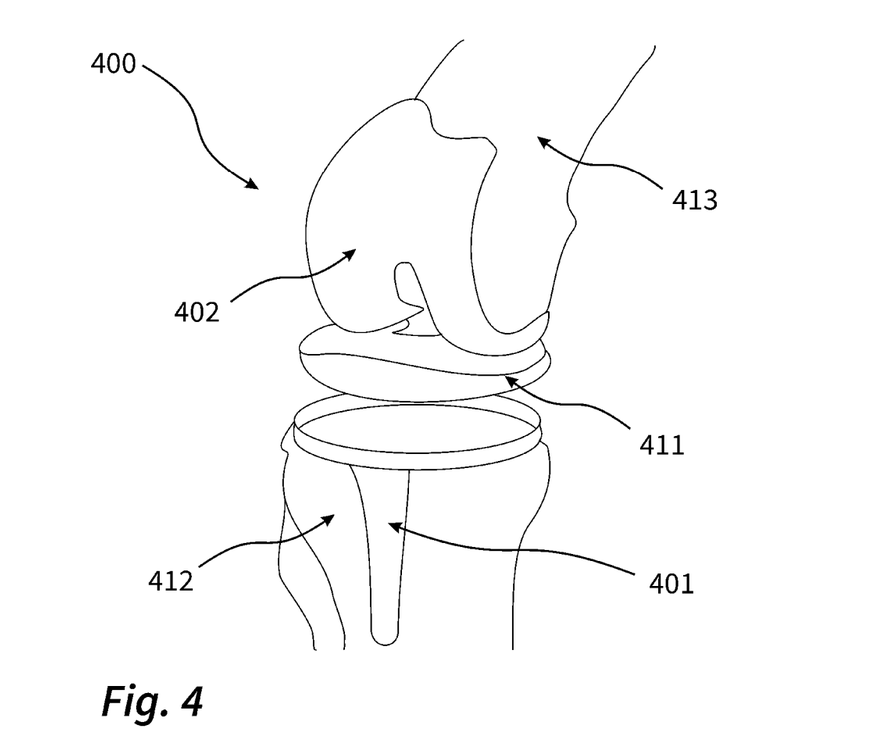
FIG. 4 is a schematic top view diagonally from the front of an artificial knee.

The implant 400 shown in FIG. 4 comprises the tibial component 401 fixed in the tibia bone 412, the femoral component 402 fixed in the femur bone 413 and the inlay 411 on which the femoral component 402 rests. While the tibia component 401 and the femur component 402 each consist of a cobalt-chromium alloy, the inlay 411 is made of ultra-high molecular polyethylene.

Figure 5:
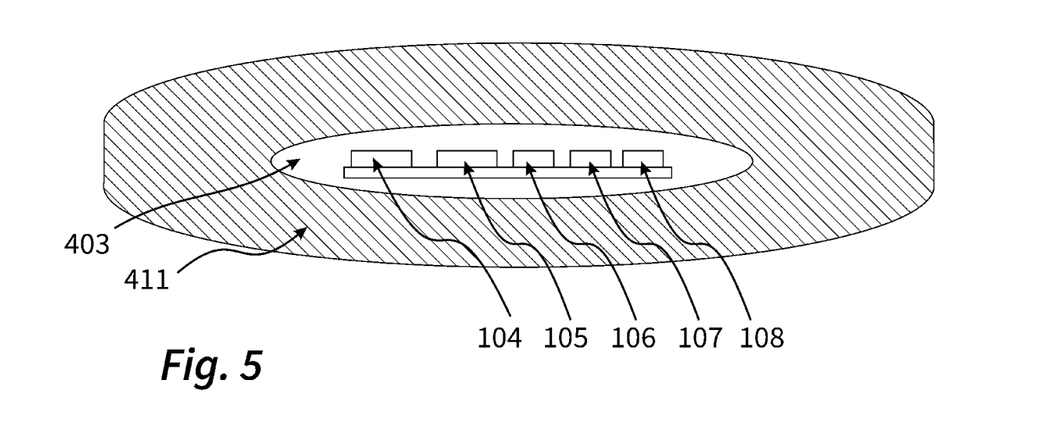
FIG. 5 is a schematic section taken through an inlay component of the knee joint shown in FIG. 4.

The section through the inlay 411 shown in FIG. 5 shows that the inlay 411 has a cavity 403. The same sensor and the same electronic components as in cavity 103 of the implant 100 are arranged in this cavity 403.

What is claimed is:

1. A method of diagnosing and/or treating inflammatory tissue after implanting an implant into a human or animal body comprising:
    a. providing the implant, wherein the implant comprises in at least one cavity:
        a sensor for detecting electromagnetic waves; and
        a data transmitter configured to wirelessly transmit data supplied by the sensor to a receiver,
    b. implanting the implant into the human or animal body,
    c. detecting, by the sensor placed in the at least one cavity of the implant, electromagnetic waves whose properties depend on a vicinity of the implant relative to a source of the electromagnetic waves or on a condition of tissue adjacent to the implant,
    d. wirelessly transmitting data supplied by the sensor with the data transmitter to the receiver,
    e. exposing the vicinity of the implant or the tissue adjacent to the implant and/or a body fluid in contact with the implant to electromagnetic radiation in a visible range of an electromagnetic spectrum and/or in an infrared range emitted from a source of light and/or radiation, and
    f. detecting the electromagnetic waves emitted or reflected from the vicinity of the implant or the tissue and/or the body fluid, by at least one light-sensitive electronic image sensor and converted into an image transmitted to the receiver by the data transmitter; wherein the implant is or comprises an artificial joint selected from the group consisting of a shoulder joint, elbow joint, wrist joint, hip joint, knee joint and ankle joint, or the implant is a pacemaker or an implantable hearing aid.

2. The method according to claim 1, further comprising: contacting the vicinity of the implant, the tissue adjacent to the implant and/or the body fluid in contact with the implant with a biochemical marker to detect inflammation, exposing the vicinity of the implant, the tissue adjacent to the implant and/or the body fluid, to the electromagnetic radiation that overlaps with an absorption and/or fluorescence spectrum of the marker, and emitting the electromagnetic radiation from the source of light and/or radiation inside the implant or outside the human or animal body.

3. The method according to claim 1, wherein the implant comprises a plastics material and wherein the sensor and the data transmitter are arranged in at least one cavity of the plastics material and wherein the plastics material is a polyolefin such as polyethylene, or a fluorinated polymer such as teflon or a polyetherketone such as polyetheretherketone.

4. The method according to claim 3, wherein
    the implant comprises the knee joint including a first portion configured to be fixed to a tibia, a second portion configured to be fixed to a femur and an inlay, on which the second portion rests, and
    the plastics material is the inlay and forms the at least one cavity in which the sensor and the data transmitter are arranged.

5. The method according to claim 1, wherein the source of light and/or radiation is positioned at one of the following locations:
    (a) inside both the implant and the human or animal body;
    (b) outside the implant and inside the human or animal body, or
    (c) outside both the implant and the human or animal body.

6. A method of diagnosing and/or treating inflammatory tissue after implanting an implant into a human or animal body comprising:
    a. providing the implant, wherein the implant comprises:
        a sensor for detecting electromagnetic waves; and
        a data transmitter configured to wirelessly transmit data supplied by the sensor to a receiver,
    b. implanting the implant including the sensor and data transmitter into the human or animal body,
    c. detecting, by the sensor, electromagnetic waves whose properties depend on a vicinity of the implant relative to a source of the electromagnetic waves or on a condition of tissue adjacent to the implant,
    d. wirelessly transmitting data supplied by the sensor with the data transmitter to the receiver,
    wherein the implant comprises a plastics, glass, ceramic or glass ceramic material and wherein the sensor and the data transmitter are arranged in at least one cavity of the plastics, glass, ceramic or glass ceramic material.

7. The method according to claim 6, wherein the implant comprises a plastics material and wherein the sensor and the data transmitter are arranged in at least one cavity of the plastics material and wherein the plastics material is a polyolefin such as polyethylene, or a fluorinated polymer such as teflon or a polyetherketone such as polyetheretherketone.

8. The method according to claim 6, wherein
    the implant comprises a knee joint including a first portion configured to be fixed to a tibia, a second portion configured to be fixed to a femur and an inlay, on which the second portion rests, and
    the plastics material is the inlay and forms the at least one cavity in which the sensor and the data transmitter are arranged.

9. A method of diagnosing and/or treating inflammatory tissue after implanting an implant into a human or animal body comprising:
    a. providing the implant, wherein the implant comprises in at least one cavity:
        a sensor for detecting electromagnetic waves; and - a data transmitter configured to wirelessly transmit data supplied by the sensor to a receiver,
    b. implanting the implant into the human or animal body,
    c. detecting, by the sensor placed in the at least one cavity of the implant, electromagnetic waves whose properties depend on a vicinity of the implant relative to a source of the electromagnetic waves or on a condition of tissue adjacent to the implant,
    d. wirelessly transmitting data supplied by the sensor with the data transmitter to the receiver,
    e. contacting the vicinity of the implant, the tissue adjacent to the implant and/or a body fluid in contact with the implant with a biochemical marker to detect inflammation,
    f. exposing the vicinity of the implant, the tissue adjacent to the implant and/or the body fluid, to electromagnetic radiation that overlaps with an absorption and/or fluorescence spectrum of the marker, and g. emitting the electromagnetic radiation from a source of light and/or radiation inside the implant or outside the human or animal body, wherein the implant is or comprises an artificial joint selected from the group consisting of a shoulder joint, elbow joint, wrist joint, hip joint, knee joint and ankle joint, or the implant is a pacemaker or an implantable hearing aid.

10. A method of diagnosing and/or treating inflammatory tissue after implanting an implant into a human or animal body comprising:
    a. providing the implant, wherein the implant comprises in at least one cavity:
       a sensor for detecting electromagnetic waves; and
       a data transmitter configured to wirelessly transmit data supplied by the sensor to a receiver,
    b. implanting the implant into the human or animal body,
    c. detecting, by the sensor placed in the at least one cavity of the implant, electromagnetic waves whose properties depend on a vicinity of the implant relative to a source of the electromagnetic waves or on a condition of tissue adjacent to the implant,
    d. wirelessly transmitting data supplied by the sensor with the data transmitter to the receiver, wherein the implant is or comprises an artificial joint selected from the group consisting of a shoulder joint, elbow joint, wrist joint, hip joint, knee joint and ankle joint, or the implant is a pacemaker or an implantable hearing aid, and the implant comprises a plastics material and wherein the sensor and the data transmitter are arranged in at least one cavity of the plastics material and wherein the plastics material is a polyolefin such as polyethylene, or a fluorinated polymer such as teflon or a polyetherketone such as polyetheretherketone.

11. A method of diagnosing and/or treating inflammatory tissue after implanting an implant into a human or animal body comprising:
    a. providing the implant, wherein the implant comprises in at least one cavity:
       a sensor for detecting electromagnetic waves; and
       a data transmitter configured to wirelessly transmit data supplied by the sensor to a receiver,
    b. implanting the implant into the human or animal body,
    c. detecting, by the sensor placed in the at least one cavity of the implant, electromagnetic waves whose properties depend on a vicinity of the implant relative to a source of the electromagnetic waves or on a condition of tissue adjacent to the implant,
    d. wirelessly transmitting data supplied by the sensor with the data transmitter to the receiver,
    e. exposing the vicinity of the implant or the tissue adjacent to the implant and/or a body fluid in contact with the implant exposed to electromagnetic radiation in a visible range of an electromagnetic spectrum and/or in an infrared range from a source of light and/or radiation, and
    f. detecting the electromagnetic waves emitted or reflected from the vicinity of the implant or the tissue and/or the body fluid, by at least one light-sensitive electronic image sensor and converted into an image transmitted to the receiver by the data transmitter; wherein the implant is or comprises an artificial joint selected from the group consisting of a shoulder joint, elbow joint, wrist joint, hip joint, knee joint and ankle joint, or the implant is a pacemaker or an implantable hearing aid, and wherein the source of light and/or radiation is positioned at one of the following locations:
    (a) inside both the implant and the human or animal body;
    (b) outside the implant and inside the human or animal body, or
    (c) outside both the implant and the human or animal body.

* * * * *